United States Patent
Meyer et al.

(10) Patent No.: US 7,276,482 B2
(45) Date of Patent: Oct. 2, 2007

(54) PEPTIDE AND PEPTIDE MIMETIC DERIVATIVES WITH INTEGRIN-INHIBITORS PROPERTIES II

(75) Inventors: Joerg Meyer, Heusenstamm (DE); Berthold Nies, Fraenkisch-Crumbach (DE); Michel Dard, Seeheim-Jugenheim (DE); Guenter Hoelzemann, Seeheim-Jugenheim (DE); Horst Kessler, Schwalbach (DE); Martin Kantlehner, Freising (DE); Ulrich Hersel, Erlabrunn (DE); Christoph Gibson, Ihringen (DE); Gabor Sulyok, Munich (DE)

(73) Assignee: Biomet Deutschland GmbH, Berlin (DE)

( * ) Notice: Subject to any disclaimer, the term of this patent is extended or adjusted under 35 U.S.C. 154(b) by 789 days.

(21) Appl. No.: 10/344,668

(22) PCT Filed: Aug. 2, 2001

(86) PCT No.: PCT/EP01/08931

§ 371 (c)(1),
(2), (4) Date: Feb. 14, 2003

(87) PCT Pub. No.: WO02/14350

PCT Pub. Date: Feb. 21, 2002

(65) Prior Publication Data

US 2004/0043937 A1    Mar. 4, 2004

(30) Foreign Application Priority Data

Aug. 17, 2000 (DE) .............................. 100 40 103

(51) Int. Cl.
    *A61K 38/10* (2006.01)
(52) U.S. Cl. ........................ 514/14; 530/327
(58) Field of Classification Search ............ None
    See application file for complete search history.

(56) References Cited

FOREIGN PATENT DOCUMENTS

| DE | 19755800 | 6/1999 |
|----|----------|--------|
| DE | 19755801 | 6/2000 |
| DE | 19831710 | 1/2001 |
| DE | 19932796 | 1/2001 |
| WO | WO92/12727 | 8/1992 |

OTHER PUBLICATIONS

[Retrieved from] http://www.elmhurst.edu/~chm/vchembook/564peptide.html, 2 pages [Retrieved on Jan. 18, 2007].*

* cited by examiner

*Primary Examiner*—Anish Gupta
*Assistant Examiner*—Satyanarayana R. Gudibande
(74) *Attorney, Agent, or Firm*—Millen, White, Zelano & Branigan, P.C.

(57) ABSTRACT

The invention relates to compounds of formula (I) B-Q-$X_1$, wherein B is a bioactive, cell adhesive mediating molecule, selected from the group (i) and Thr-Trp-Tyr-Lys-Ile-Ala-Phe-Gln-Arg-Asn-Arg-Lys (SEQ ID NO: 1) (ii), Trp-Tyr-Lys-Ile-Ala-Phe-Gln-Arg-Asn-Arg-Lys (SEQ ID NO: 2) (iii), Tyr-Lys-Ile-Ala-Phe-Gln-Arg-Asn-Arg-Lys (SEQ ID NO: 3) (iv), Thr-Trp-Tyr-Lys-Ile-Ala-Phe-Gln-Arg-Asn-Arg (SEQ ID NO: 4) (v), Thr-Trp-Tyr-Lys-Ile-Ala-Phe-Gln-Arg-Asn (SEQ ID NO: 5) (vi), Thr-Trp-Tyr-Lys-Ile-Ala-Phe-Gln-Arg (SEQ ID NO: 6) (vii), wherein (i) X, Y, Z, $R^2$, $R^3$, $R^4$, A, Ar, Hal, Het, $Het^1$, n, m, o, p, q, s, t have the meanings cited in claim 1, Q is absent or is an organic spacer molecule, $X_1$ is an anchor molecule selected from the group cited in claim 1, and the salts thereof, which can be used as integrin inhibitors particularly for treatment of illness, deficiencies and inflammations caused by implants and osteolytic illnesses such as osteoporosis, thrombosis, cardiac infarction and arteriosclerosis, in addition to the acceleration and strengthening of the integration process of implants or the biocompatible surface in tissue.

11 Claims, No Drawings

SEQUENCE LISTING

```
<160> NUMBER OF SEQ ID NOS: 12

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Thr Trp Tyr Lys Ile Ala Phe Gln Arg Asn Arg Lys
 1               5                  10

<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Trp Tyr Lys Ile Ala Phe Gln Arg Asn Arg Lys
 1               5                  10

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Tyr Lys Ile Ala Phe Gln Arg Asn Arg Lys
 1               5                  10

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Thr Trp Tyr Lys Ile Ala Phe Gln Arg Asn Arg
 1               5                  10
```

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Thr Trp Tyr Lys Ile Ala Phe Gln Arg Asn
 1               5                  10

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Thr Trp Tyr Lys Ile Ala Phe Gln Arg
 1               5

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(14)
<223> OTHER INFORMATION: Aca

<400> SEQUENCE: 7

Thr Trp Tyr Lys Ile Ala Phe Gln Arg Asn Arg Lys Xaa Xaa Cys
 1               5                  10                  15

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Aca

<400> SEQUENCE: 8

Cys Xaa Xaa Thr Trp Tyr Lys Ile Ala Phe Gln Arg Asn Arg Lys
 1               5                  10                  15

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(11)
<223> OTHER INFORMATION: Aca

<400> SEQUENCE: 9

```
Lys Ile Ala Phe Gln Arg Asn Arg Lys Xaa Xaa Cys
 1               5                  10
```

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Aca

<400> SEQUENCE: 10

```
Cys Xaa Xaa Thr Trp Tyr Lys Ile Ala Phe Gln Arg
 1               5                  10
```

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(8)
<223> OTHER INFORMATION: Aca

<400> SEQUENCE: 11

```
Phe Gln Arg Asn Arg Lys Xaa Xaa Cys
 1               5
```

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Aca

<400> SEQUENCE: 12

```
Cys Xaa Xaa Thr Trp Tyr Lys Ile Ala
 1               5
```

PEPTIDE AND PEPTIDE MIMETIC DERIVATIVES WITH INTEGRIN-INHIBITORS PROPERTIES II

The invention relates to compounds of the formula I

B-Q-$X_1$     I in which
B is a bioactive, cell adhesion-mediating molecule, selected from the group

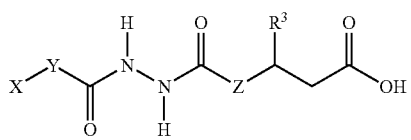
(i)

And (SEQ ID NOS 1-6, respectively in order of appearance)

Thr-Trp-Tyr-Lys-Ile-Ala-Phe-Gln-Arg-Asn-Arg-Lys (ii)

Trp-Tyr-Lys-Ile-Ala-Phe-Gln-Arg-Asn-Arg-Lys (iii)

Tyr-Lys-Ile-Ala-Phe-Gln-Arg-Asn-Arg-Lys (iv)

Thr-Trp-Tyr-Lys-Ile-Ala-Phe-Gln-Arg-Asn-Arg (v)

Thr-Trp-Tyr-Lys-Ile-Ala-Phe-Gln-Arg-Asn (vi)

Thr-Trp-Tyr-Lys-Ile-Ala-Phe-Gln-Arg (vii), where for (i)
X is $H_2N-C(=NH)-NH$, Het-NH—, $H_2N-C(=NH)-$, A-C(=NH)—NH— or Het-,
Y is —$(CH_2)_n$— or 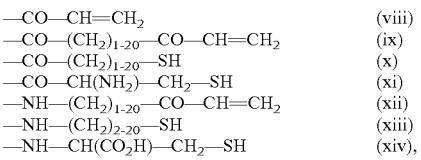

—$(CH_2)_s$—CH($R^4$)—$(CH_2)_t$—   or   —$(CH_2)_p$-$Het^2$-$(CH_2)_q$—,

Z is N—$R^2$ or CH—$R^2$,
$R^2$ is H or alkyl having 1 to 4 C atoms,
$R^3$ is H, Ar, Het or A,
$R^4$ is H, A, Ar, OH, OA, OAr, arylalkyl, Hal, CN, $NO_2$, $CF_3$ or $OCF_3$,
A is COOH, $NH_2$ or alkyl having 1-6 C atoms, which is unsubstituted or substituted by COOH or $NH_2$,
Ar is phenyl which is unsubstituted or mono-, di- or trisubstituted by A, OH, $NH_2$, OA, $CF_3$, $OCF_3$, CN, $NO_2$ or Hal, which can be substituted by a phenyl which is mono-, di- or trisubstituted by A, OH, OA, $OCF_3$, CN, $NO_2$ or Hal in such a way that an unsubstituted or substituted biphenyl results,
Hal is F, Cl, Br or I, Het is a saturated, partly or completely unsaturated mono- or bicyclic heterocyclic radical having 5 to 10 ring members, where 1 to 3 N and/or an S or O atom(s) can be present and the heterocyclic radical can be mono- or disubstituted by CN, Hal, OH, $NH_2$, COOH, OA, $CF_3$, A, $NO_2$, Ar or $OCF_3$,
$Het^2$ is a 5- or 6-membered aromatic heterocycle having 1 to 4 N and/or S atoms, which can be unsubstituted or mono- or disubstituted by F, Cl, Br, A, OA or $OCF_3$,
n is 4, 5 or 6,
m, o, p, q are 0, 1 or 2,
s, t are 0, 1, 2, 3, 4, 5;
Q is absent or is an organic spacer molecule and
$X_1$ is an anchor molecule, selected from the group

| | |
|---|---|
| —CO—CH=$CH_2$ | (viii) |
| —CO—$(CH_2)_{1-20}$—CO—CH=$CH_2$ | (ix) |
| —CO—$(CH_2)_{1-20}$—SH | (x) |
| —CO—CH($NH_2$)—$CH_2$—SH | (xi) |
| —NH—$(CH_2)_{1-20}$—CO—CH=$CH_2$ | (xii) |
| —NH—$(CH_2)_{2-20}$—SH | (xiii) |
| —NH—CH($CO_2H$)—$CH_2$—SH | (xiv), | where in the case of the compounds (viii) to (xi) a free amino group of the group B with [sic] a free carboxyl group of the spacer molecule Q or of the anchor molecule $X_1$ or a free amino group of the radical Q with [sic] a free carboxyl group of the radical $X_1$ is [sic] linked to one another like peptides, and in the case of the compounds (xii) to (xiv) a free carboxyl group of the group B with [sic] a free amino group of the spacer molecule Q or of the anchor molecule $X_1$ or a free carboxyl group of the radical Q with [sic] a free amino group of the radical $X_1$ are linked to one another like peptides, and their salts.

Similar compounds are disclosed in DE 19932796, DE 19755800 and DE 19831710.

The invention was based on the object of finding novel compounds having valuable properties, in particular those which can be used for the production of medicaments.

It has been found that the compounds of the formula I and their salts have very valuable pharmacological properties, together with good tolerability. They act especially as integrin inhibitors, inhibiting, in particular, the interactions of the $\alpha_v$, $\beta_3$ or $\beta_5$ integrin receptors with ligands, e.g. the binding of fibrinogen to the $\beta_3$ integrin receptor. The compounds show particular activity in the case of the integrins $\alpha_v\beta_3$, $\alpha_v\beta_5$, $\alpha_{IIb}\beta_3$, $\alpha_v\beta_1$, $\alpha_v\beta_6$ and $\alpha_v\beta_8$.

This action can be demonstrated, for example, according to the method which is described by J. W. Smith et al. in J. Biol. Chem. 265, 12267-12271 (1990).

The dependence of the development of angiogenesis on the interaction between vascular integrins and extra-cellular matrix proteins is described by P. C. Brooks, R. A. Clark and D. A. Cheresh in Science 264, 569-71 (1994).

Compounds of the formula I which block the interaction of integrin receptors and ligands, e.g. of fibrinogen to the fibrinogen receptor (glycoprotein IIb/IIIa), prevent, as GPIIb/IIIa antagonists, the spread of tumour cells by metastasis. This is confirmed by the following observations: the spread of tumour cells from a local tumour into the vascular system takes place through the formation of microaggregates (microthrombi) by interaction of the tumour cells with blood platelets. The tumour cells are screened by the protection in the microaggregate and are not recognized by the cells of the immune system. The microaggregates can attach to vessel walls, owing to which further penetration of tumour cells into the tissue is facilitated.

Since the formation of the microthrombi is mediated by fibrinogen binding to the fibrinogen receptors on activated blood platelets, the GPIIa/IIIb antagonists can be regarded as effective metastasis inhibitors.

The (meth)acrylic radical serves to bind the peptides and peptide mimetics covalently or adsorptively to biocompatible surfaces of, for example, implants which contain free acrylate or methacrylate radicals, e.g. polymethylmethacrylic shaped articles (bone cement) or acrylate- or methacrylate-containing layers, e.g. on metal surfaces.

Correspondingly, the thiol radical serves to bind the peptide, for example, to gold surfaces or to free amino group-containing surfaces such as collagen (e.g. by means of maleimide), with plasma-treated polymer or metal surfaces (see D. M. Ferris, G. D. Moodie, P. M. Dimond, C. W. D. Giovanni, M. G. Ehrlich, R. F. Valentini, Biomaterials 20, 2323-2331 (1999); D. F. Meyers et al., J. Immunol. Methods 121, 129-142 (1989)) or with surfaces treated by the CVD technique (see Lahann, J. et al., Macromol. Rapid Commun. 19, 441-444 (1998)).

The invention therefore relates to the compounds of the formula I for covalent or adsorptive binding via the functional group of the radical $X_1$ to biocompatible surfaces.

In this connection, reference is made to the second application filed by the applicant on the same date, in which the radical $X_1$ has another meaning.

The peptides and peptide mimetics according to the invention now make possible the biofunctionalization of biomaterials, in particular implants for all conceivable organs, by means of coating thereof, mainly the adhesion of those cell species being stimulated which should in each case effect the tissue integration of the corresponding biomaterial. Using such coatings, an accelerated and enhanced integration of various biomaterials/implants with improved long-term stability after their incorporation into the body can be achieved.

The peptides according to the invention bind selectively to integrins. After immobilization on biocompatible surfaces, e.g. implants, they stimulate the adhesion of cells which carry integrins.

After coating of the compounds on the surfaces, those cell species can selectively be stimulated to binding which should also effect the implant integration after implantation in the natural tissue. In osteoblasts, osteoclasts and endothelial cells these are, for example, $\alpha_v$-carrying cell species.

The invention therefore relates to the compounds of the formula I as integrin inhibitors for selective cell enrichment in implants.

After anchoring to a biocompatible surface as pharmaceutical active compounds, the compounds of the formula I can be employed in human and veterinary medicine, in particular they can be employed as integrin inhibitors for the treatment of disorders, defects and inflammations caused by implants, such as inadequate and delayed integration of biomaterials and implants, of thrombosis caused by implants, of bone and tooth defects, and of osteolytic disorders such as osteoporosis, thrombosis, cardiac infarct, arteriosclerosis, in wound healing for assisting the healing process, and also for the acceleration and strengthening of the integration process of the implant or of the biocompatible surface into the tissue.

The compounds of the formula I can be employed as substances having antimicrobial action in operations where biomaterials, implants, catheters or cardiac pacemakers are used. They have an antiseptic action here. The efficacy of the antimicrobial activity can be demonstrated by the procedure described by P. Valentin-Weigund et al., in Infection and Immunity, 2851-2855 (1988).

The invention thus relates to the compounds of the formula I as integrin inhibitors for the treatment of disorders, defects and inflammations caused by implants, and of osteolytic disorders such as osteoporosis, thrombosis, cardiac infarct and arteriosclerosis, and also for the acceleration and strengthening of the integration process of the implant or of the biocompatible surface into the tissue.

The invention further relates to the use of compounds of the formula I for the production of a medicament for the treatment of disorders, defects and inflammations caused by implants, and of osteolytic disorders such as osteoporosis, thrombosis, cardiac infarct and arteriosclerosis, and for the acceleration and strengthening of the integration process of the implant or of the biocompatible surface into the tissue.

Corresponding peptides carrying thiol anchors can be bonded covalently to gold-plated carriers, such as implants, affinity chromatographies [sic] or microtitre plates.

The invention also relates to the use of compounds of the formula I for the coating, by means of covalent or adsorptive binding, of implants for human and animal organs.

The abbreviations of amino acid residues mentioned above and below stand for the radicals of the following amino acids:

| | |
|---|---|
| Abu | 4-aminobutyric acid |
| Aha | 6-aminohexanoic acid, 6-aminocaproic acid |
| Ala | alanine |
| Asn | asparagine |
| Asp | aspartic acid |
| Arg | arginine |
| Cys | cysteine |
| Dab | 2,4-diaminobutyric acid |
| Dap | 2,3-diaminopropionic acid |
| Gln | glutamine |
| Glp | pyroglutamic acid |
| Glu | glutamic acid |
| Gly | glycine |
| His | histidine |
| homo-Phe | homo-phenylalanine |
| Ile | isoleucine |
| Leu | leucine |
| Lys | lysine |
| Met | methionine |
| Nle | norleucine |
| Orn | ornithine |
| Phe | phenylalanine |
| Phg | phenylglycine |
| 4-Hal-Phe | 4-halophenylalanine |
| Pro | proline |
| Ser | serine |
| Thr | threonine |
| Trp | tryptophan |
| Tyr | tyrosine |
| Val | valine. |

In addition, the abbreviations below have the meanings:

| | |
|---|---|
| Ac | acetyl |
| BOC | tert-butoxycarbonyl |
| CBZ or Z | benzyloxycarbonyl |
| DCCI | dicyclohexylcarbodiimide |
| DMF | dimethylformamide |
| EDCI | N-ethyl-N,N'-(dimethylaminopropyl)carbodi-imide |
| Et | ethyl |
| FCA | fluoresceincarboxylic acid |
| FITC | fluorescein isothiocyanate |
| Fmoc | 9-fluorenylmethoxycarbonyl |
| FTH | fluoresceinthiourea |
| HATU | O-7-azabenzotriazol-1-yl)-N,N,N',N'-tetramethyluronium hexafluorophosphate |
| HOBt | 1-hydroxybenzotriazole |
| Me | methyl |
| MBHA | 4-methylbenzhydrylamine |
| Mtr | 4-methoxy-2,3,6-trimethylphenylsulfonyl |
| HONSu | N-hydroxysuccinimide |
| OtBu | tert-butyl esther |
| Oct | octanoyl |
| OMe | methyl ester |
| OEt | ethyl ester |
| POA | phenoxyacetyl |
| Pbf | pentamethylbenzofuranyl |
| Pmc | 2,2,5,7,8-pentamethylchroman-6-sulfonyl |
| Sal | salicyloyl |
| Su | succinyl |
| TFA | trifluoroacetic acid |
| Trt | trityl (triphenylmethyl). |

If the abovementioned amino acids can occur in a number of enantiomeric forms, all these forms and their mixtures (e.g. the DL forms) are included above and below, e.g. as part of the compounds of the formula I. In addition, amino acids or the free amino group (xi) or the free carboxyl group (xiv), as part of compounds of the formula I, can be provided with corresponding protective groups which are known per se.

Above all, side chain modifications of arginine, such as were carried out, for example, in the case of the non-peptide $\alpha_v\beta_3$ antagonists (e.g. by R. Keenan et al., Abstr. Pap. 211th ACS National Meeting (New Orleans, USA) 1996, MEDI 236), can also be employed in the case of the cyclopeptides, e.g. benzimidazole derivatives instead of the guanidine group.

"Prodrug derivatives" are also included in the compounds according to the invention, i.e. compounds of the formula I modified with, for example, alkyl or acyl groups, sugars or oligopeptides, which are rapidly cleaved in the body to give the active compounds according to the invention.

These also include biodegradable polymer derivatives of the compounds according to the invention, as is described, for example, in Int. J. Pharm. 115, 61-67 (1995).

The invention further relates to an implant which is suitable for human and animal organs, consisting of a carrier matrix and a layer of a bioactitve, cell adhesion-mediating molecule surrounding this matrix, the surrounding layer being formed from a compound of the formula I, and a covalent or adsorptive bond being present between carrier matrix and this compound. Preferably, the carrier matrix and/or its surface consists of a metal or metal oxide or a polymer. Suitable polymers are preferably polymethyl methacrylate, polyhydroxyethyl methacrylate, polylactite [sic], polyglycolic acid or copolymers thereof.

The invention further relates to a process for the preparation of compounds of the formula I according to claim 1, and of their salts, characterized in that a bioactive molecule B, which can be provided with protective groups, and a spacer-anchor molecule (Q-$X_1$) or anchor molecule ($X_1$) provided with protective groups are linked to one another in peptide fashion and the protective groups are then removed, and/or in that a basic or acidic compound of the formula I is converted into one of its salts by treating with an acid or base.

Above and below, the radicals B, Q and $X_1$ have the meaning indicated under the formula I, if not expressly stated otherwise.

Q is absent or is an organic spacer molecule. Preferably, this is a [CO—($CH_2$)$_x$NH—]$_m$—, [CO—$CH_2$—(O—$CH_2CH_2$)$_y$—NH—]$_m$—, [CO—($CH_2$)$_z$—CO—]—, [NH—($CH_2$)$_z$—NH—]—, [CO—$CH_2$—(O$CH_2CH_2$)$_y$—O—$CH_2$—CO—]— or an [NH—$CH_2CH_2$—(O$CH_2CH_2$)$_y$—NH—] — radical, and their combinations, where the ranges of values specified in claim 2 apply to the indices m, x, y and z. The abovementioned compounds which can assume values between 1 and 8 for m, values between 1 and 5 for x and values between 1 and 6 for y and z have proved particularly advantageous.

$X_1$ is an anchor molecule, preferably from the group —CO—CH=$CH_2$, —CO—($CH_2$)$_{1-20}$—CO—CH=$CH_2$, —CO—($CH_2$)$_{1-20}$—SH, —CO—CH($NH_2$)—$CH_2$—SH, —NH—($CH_2$)$_{1-20}$—CO—CH=$CH_2$, —NH—($CH_2$)$_{2-20}$—SH or —NH—CH($CO_2H$)—$CH_2$—SH.

X is preferably $H_2N$—C(=NH)—NH—, Het-NH—, $H_2N$—C(=NH)—, A-C(=NH)—NH or a Het radical.

Y is preferably, —($CH_2$)$_n$— or

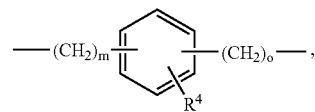

—($CH_2$)$_s$—CH($R^4$)—($CH_2$)$_t$— or —($CH_2$)$_p$-$Het^2$-($CH_2$)$_q$— radical.

Z is preferably N—$R^2$ or CH—$R^2$, where $R^2$ can preferably be an H atom or alkyl radical having 1 to 4 C atoms.

$R^3$ is preferably an H atom, Ar, Het or A radical, where A, Ar and Het have one of the meanings indicated previously or below.

$R^4$ is preferably an H atom, A, Ar, OH, OA, OAr, arylalkyl, Hal, CN, $NO_2$ $CF_3$ or $OCF_3$ radical. Arylalkyl is preferably benzyl, phenylethyl, phenylpropyl or naphthylmethyl, particularly preferably benzyl.

A is preferably a COOH, $NH_2$ or alkyl radical having 1 to 6, preferably 1, 2, 3, 4, 5 or 6, C atoms, which is unsubstituted or substituted by COOH or $NH_2$. A is preferably methyl, furthermore ethyl, propyl, n-butyl, isobutyl, sec-butyl or tert-butyl, in addition also n-pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl. A is particularly preferably methyl.

Ar is preferably phenyl which is unsubstituted or mono-, di- or trisubstituted by A, OH, OA, CF$_3$, OCF$_3$, CN, NO$_2$ or Hal, which can be substituted by phenyl which is mono-, di- or trisubstituted by A, OH, OA, NH$_2$, OCF$_3$, CN, NO$_2$ or Hal in such a way that an unsubstituted or substituted biphenyl results.

Ar is therefore preferably phenyl, o-, m- or p-methylphenyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-methoxyphenyl, o-, m- or p-ethoxyphenyl, o-, m-, p-trifluoromethylphenyl, o-, m-, p-trifluoromethoxyphenyl, o-, m- or p-fluorophenyl, o-, m- or p-chlorophenyl, o-, m- or p-bromophenyl, o-, m- or p-nitrophenyl.

Het is a saturated, partly or completely unsaturated mono- or bicyclic heterocyclic radical having 5 to 10 ring members, where 1 to 3 N and/or 1 S or O atom(s) can be present and the heterocyclic radical can be mono- or disubstituted by CN, Hal, OH, NH$_2$, COOH, OA, CF$_3$, A, NO$_2$, Ar or OCF$_3$.

Het is preferably an o-, m- or p-substituted pyridyl, a 2-, 4-, 5- or 6-substituted pyrimidyl or a 3-, 4-, 5- or 6-substituted pyridazyl which is preferably unsubstituted or substituted by a methyl, ethyl or propyl group or a methylamino, ethylamino or propylamino group [relates to all of the three heteroaromatics mentioned], and also a 2-substituted benzimidazolyl which is unsubstituted or substituted by a 3-methyl, 3-ethyl or 3-benzyl group, and also a 2-substituted dihydroimidazolyl, tetrahydropyrimidyl or tetrahydropyridyl.

Examples which are preferably contained in Het are:

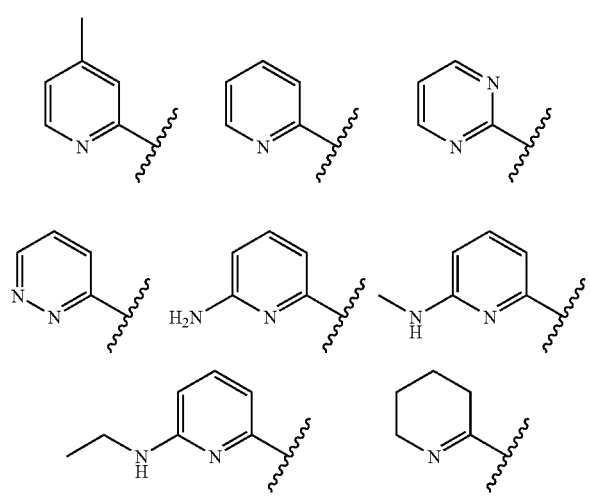

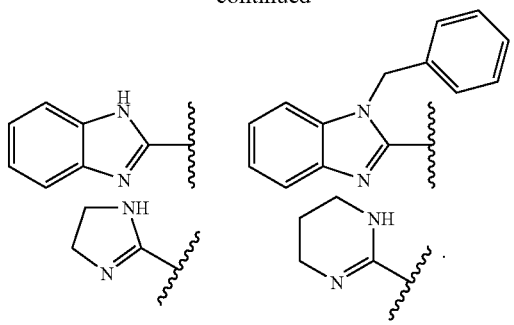

Het$^1$ is a 5- or 6-membered aromatic heterocycle having 1 to 4 N and/or S atoms, which can be unsubstituted or mono- or disubstituted by F, Cl, Br, A, OA or OCF$_3$.

Het$^1$ is preferably a 2,4-, 3,5- or 2,5-disubstituted pyridyl or a 2,4-, 2,5-, 2,6- or 4,6-disubstituted pyrimidyl, a 2,4- or 2,5-disubstituted 1,3-oxazolyl or 1,3-thiazolyl.

OA is preferably methoxy, ethoxy, propoxy or butoxy, in addition also pentyloxy or hexyloxy.

Hal is preferably F, Cl or Br, but also I.

The indices n, m, o, p, q, s and t have the meaning indicated in claim 1, if not expressly stated otherwise.

The compounds of the formula I can have one or more chiral centres and therefore occur in various stereoisomeric forms. The formula I includes all these forms.

Accordingly, the invention relates in particular to those compounds of the formula I in which at least one of the radicals mentioned has one of the preferred meanings indicated above.

Particularly preferred compounds of the formula I are the following: (SEQ ID NOS 7-12, respectively in order of appearance)

a) 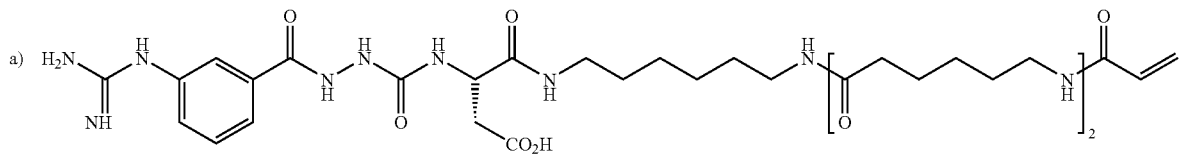

The compounds of the formula I and also the starting substances for their preparation are otherwise prepared by methods known per se, such as are described in the literature (e.g. in the standard works such as Houben-Weyl, Methoden der organischen Chemie [Methods of Organic Chemistry], Georg-Thieme-Verlag, Stuttgart or The Journal of Biological Chemistry, Vol. 271, No. 44, pp. 27221 ff. (1996)), namely under reaction conditions which are known and suitable for the reactions mentioned. Use can also be made in this case of variants which are known per se, but not mentioned here in greater detail.

If desired, the starting substances can also be formed in situ such that they are not isolated from the reaction mixture, but immediately reacted further to give the compounds of the formula I.

The fragment coupling is carried out in an inert solvent, a carboxylic acid fragment (acrylate or thiol linker) being dissolved in DMF with HATU, HOAt and 2,4,6-collidine and then treated with the amine fragment (linear peptide, peptide mimetic) or alternatively conversely (linker=amine fragment; peptide/mimetic=carboxylic acid fragment).

Suitable inert solvents are, for example, hydrocarbons such as hexane, petroleum ether, benzene, toluene or xylene; chlorinated hydrocarbons such as trichloroethylene, 1,2-dichloroethane, carbon tetrachloride, chloroform or dichloromethane; alcohols such as methanol, ethanol, isopropanol, n-propanol, n-butanol or tert-butanol; ethers such as diethyl ether, diisopropyl ether, tetrahydrofuran (THF) or dioxane; glycol ethers such as ethylene glycol monomethyl or monoethyl ether (methyl glycol or ethyl glycol), ethylene glycol dimethyl ether (diglyme); ketones such as acetone or butanone; amides such as acetamide, N-methylpyrrolidone, dimethylacetamide or dimethylformamide (DMF); nitriles such as acetonitrile; sulfoxides such as dimethyl sulfoxide (DMSO), carbon disulfide; carboxylic acids such as formic acid or acetic acid; nitro compounds such as nitromethane or nitrobenzene; esters such as ethyl acetate, water or mixtures of the solvents mentioned.

General Working Techniques:

The reagents were obtained from the companies Aldrich, Bachem, Fluka, Neosystem and Novabiochem and used without further purification. The trityl chloride/polystyrene resin (TCP resin) came from the company PepChem.

(RP9) HPLC analysis and semi-preparative separations were carried out on equipment from the companies Waters and Beckman using a UV detector (Uvicord) from Knauer and Amersham Pharmacia Biotech. The UV detection was carried out at the wavelength 220 nm. The following column materials were used for the analysis (diameter 4 mm) and semi-preparative separation (diameter 21 mm or 40 mm): Nucleosil RP18 5μ, Nucleosil RP18 HD 5μ and Nucleosil RP18 7μ from Macherey & Nagel). As eluent, mobile phase mixtures of acetonitrile and water in each case containing 0.1% by volume of TFA were used under gradient operation conditions.

The ESI mass spectra were carried out using an apparatus from the company Finnigan of the LCQ type.

NMR spectra were recorded on a Bruker DMX 500. The internal standard for chemical shifts of $^1$H and $^{13}$C was the solvent of [sic] DMSO-$d_5$: 2.49 ppm ($^1$H-NMR) and 39.5 ppm ($^{13}$C-NMR)

The solid-phase syntheses were carried out in 10 ml plastic syringes having PP frits from the company Vetter-Laborbedarf (Tübingen). For the thorough mixing of the resin suspensions, the plastic syringes were rotated end over end at about 15 rpm.

The reactions of the activated azaGly and the guanylations on the solid phase were carried out with exclusion of atmospheric moisture.

The following example describes the compounds according to the invention by means of the multistage synthesis of an aza-RGD mimetic having an acrylate anchor.

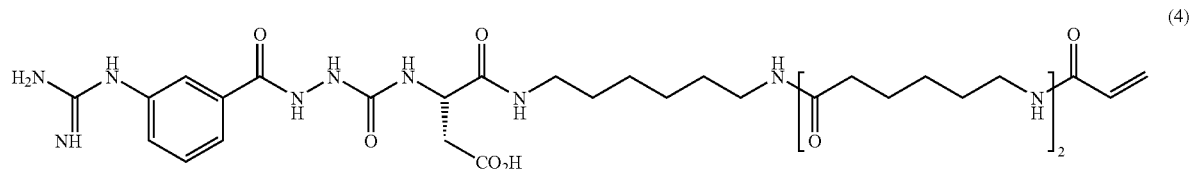

(4)

EXAMPLE 1

Synthesis of
Gua-Mab-azaGly-Asp-Hda-εAhx-εAhx-Aca (4)

Gua(Boc)$_2$-Mab-azaGly-Asp(Bu)-OH (1)

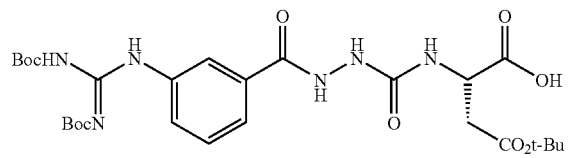

(1)

Asp(Bu)-TCP resin (1.00 g, 0.6 mmol/g, 0.6 mmol) afforded, after a multistage known synthesis (see Gibson, C.; Goodman, S. L.; Hahn, D.; Hölzemann, G.; Kessler, H. Novel Solid-Phase Synthesis of Azapeptides and Azapeptoides [sic] via Fmoc-Strategy and its Application in the Synthesis of RGD-Mimetics. J. Org. Chem. 1999, 64, 7388-7394 and Gibson, C.; Kessler, H. 2-fluoropyrimidine as an efficient reagent in solid-phase synthesis of N-aryl- and N-alkyl-N-pyrimidin-2-ylamines. Tetrahydron Lett. 2000, 41, 1725-1728), the compound 1 (75.5 mg, 21% crude yield) as a colourless oil.

HPLC (10-90% in 30 min) $R_t$=21.9 min; ESI-MS: m/z 1239.1 (30) [2M+Na$^+$], 1217.0 (30) [2M+H$^+$], 631.1 (30) [M+Na$^+$], 609.0 (100) [M+H$^+$].

Gua(Boc)$_2$-Mab-azaGly-Asp(Bu)-Hda-H (2):

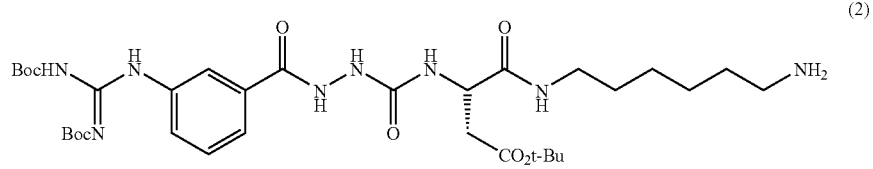

(2)

Gua(Boc)$_2$-Mab-azaGly-Asp(Bu)-OH (1) (75.2 mg, 0.123 mmol), HOAt [sic] (16.8 mg, 0.124 mmol, 1.0 equiv.) and HATU (56.5 mg, 0.148 mmol, 1.2 equiv.) were dissolved in anhydrous DMF (1.5 ml) and then treated with collidine (163 μl, 149 mg, 1.23 mmol, 10 equiv.). After 2 h, this solution was added dropwise with vigorous stirring at 10° C. in the course of 5 min to a solution of 1,6-diaminohexane (0.287 g, 2.47 mmol, 20 equiv.) in DMF (2 ml). The reaction was left at this temperature for 10 min and then stirred at room temperature for a further 70 min. The reaction mixture was then concentrated in an oil pump vacuum. The residue was taken up in CH$_2$Cl$_2$ (15 ml) and extracted with H$_2$O (2×15 ml). Concentration in vacuo afforded the compound 2 (82.2 mg, 95% crude yield) as a brown solid.

HPLC (10-90% in 30 min) R$_t$=20.1 min; ESI-MS: m/z 1435.2 (30) [2M+Na$^+$], 1413.2 (30) [2M+H$^+$], 729.2 (60) [M+Na$^+$], 707.2 (100) [M+H$^+$].

2:1 Mixture of Gua(Boc)-Mab-azaGly-Asp(Bu)-Hda-εAhx-εAhx-Aca (3a) and Gua(Boc)$_2$-Mab-azaGly-Asp(Bu)-Hda-εAhx-εAhx-Aca (3b)

afforded a mixture of 3a and 3b in the HPLC integral ratio of 2:1 (33.9 mg, 32%) as a colourless solid.

3a:

HPLC (10-90% in 20 min) R$_t$=11.8 min; ESI-MS: m/z 909.3 (70) [M+Na$^+$], 887.3 (40) [M+H$^+$].

3b:

HPLC (10-90% in 20 min) R$_t$=16.8 min; ESI-MS: m/z 1009.3 (90) [M+Na$^+$].

Gua-Mab-azaGly-Asp-Hda-εAhx-εAhx-Aca (4):

A 2:1 mixture of 3a and 3b (33 mg, 36 μmol) was suspended in CH$_2$Cl$_2$ (0.5 ml) and then treated with a 95:5 TFA/H$_2$O mixture. After 1 h, the reaction mixture was concentrated in vacuo. Lyophilization from H$_2$O afforded the compound 4 (29.0 mg, 95%, contaminated with 10% of the deguanylated compound) as a colourless solid.

$^1$H-NMR (500 MHz, DMSO): δ=10.31 (s, 1H, Ar—CO—NH—NH), 10.02 (s, 1H, NH—Ar), 8.24 (s, 1H, Ar—CO—NH—NH), 8.04 (m$_c$, 1H, CO—NH) 7.77 (d, J=7.8 Hz, 1H, arom), 8.24-7.50 (m, 8H, 2×Ar—H, H$_2$N—CNH$_2$—NH, 2×CO—NH), 7.41 (d, J=7.9 Hz, 1H, arom), 7.17-17.09 (m, 1H, CO—NH), 6.80 (br. s, 1H, NH—NH—CO—NH), 6.19 (dd, J=17.2, 10.1 Hz, 1H, CO—CH=CH$_2$), 6.04 (dd,

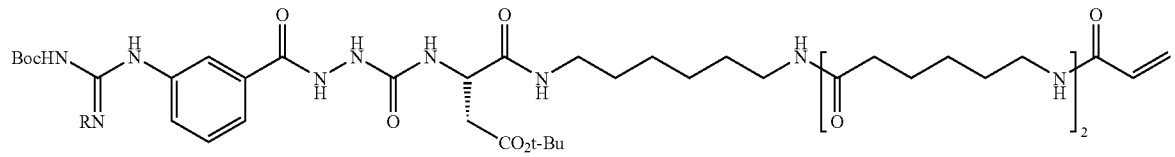

3a R = H
3b R = Boc 6-([6-(Allanoylamino)hexanoyl]amino)hexanoic acid (Aca-εAhx-εAhx-OH) (69 mg, 0.23 mmol, 2.0 equiv.) and HATU (97 mg, 0.26 mmol, 2.2 equiv.) were dissolved in anhydrous DMF (2.5 ml) and then treated with collidine (340 μl, 310 mg, 2.6 mmol, 22 equiv.). After 1 h, a solution of Gua(Boc)$_2$-Mab-azaGly-Asp(Bu)-Hda-H (2) (82.0 mg, 0.116 mmol) in DMF (1 ml) was added dropwise with stirring in the course of 5 min. After 2 h, the reaction mixture was concentrated in an oil pump vacuum. The residue was taken up in a solvent mixture of CH$_2$Cl$_2$ (1 ml) and TFE (250 μl) and slowly added dropwise to CH$_3$CN (35 ml). A colourless precipitate was formed, which was removed by centrifugation and decantation. Removal of the solvent in vacuo and purification by HPLC (30-80% in 30 min)

J=17.1, 2.1 Hz, 1H, CO—CH=CH$^{cis}$H$^{trans}$), 5.54 (dd, J=10.1, 2.1 Hz, 1H, CO—CH=CH$^{cis}$H$^{trans}$), 4.42 (dt, J=J'=7.9 Hz, 1H, NH—CH—CO), 3.13-2.94 (m, 8H, 4×CO—NH—CH$_2$) AB signal (δ$_A$=2.63, δ$_B$=2.55, J$_{AB}$=16.1, additionally split by J$_{A,H(\alpha)}$=5.4 Hz and J$_{B,H(\alpha)}$=7.2 Hz, 2H, CH—CH$_2$—CO$_2$H), 2.01 (t, J=7.3 Hz, 4H, 2×CO—CH$_2$), 1.51-1.15 (m, 20H, aliphat.); $^{13}$C-NMR (125.0 MHz, DMSO): δ=172.0, 171.83, 171.76, 170.6, 164.4, 157.6, 155.8, 135.6, 133.9, 131.9, 129.8, 127.6, 125.3, 124.7, 123.4, 50.1, 38.7, 38.4, 38.3, 38.2, 35.3, 29.0, 28.9, 28.8, 26.1, 25.9, 25.0; HPLC (10-80% in 30 min) R$_t$=10.6 min; ESI-MS: m/z 753.3 (10) [M+Na$^+$], 731.3 (100) [M+H$^+$].

Example for Cell Adhesion Test

The adhesion of mouse MC3T3 H1 osteoblast cultures in vitro to peptide-coated material surfaces was investigated. In this test, 50 000 cells/cm$^2$ were inoculated and, after incubation in serum-free medium at 37° C./95% atmospheric humidity for one hour, the proportion of adhered cells was determined.

Cell adhesion rate [%]=adhered cells/inoculated cells×100

Peptide: cell adhesion rate [%]
Gua-Mab-azaGly-Asp-Hda-εAhx-εAhx-Aca: 75
Thr-Trp-Tyr-Lys-Ile-Ala-Phe-Gln-Arg-Asn-Arg-Lys-Aca-Aca-Cys: 105 (SEQ ID NO: 7)
Cys-Aca-Aca-Thr-Trp-Tyr-Lys-Ile-Ala-Phe-Gln-Arg-Asn-Arg-Lys: 101 (SEQ ID NO: 8)
Lys-Ile-Ala-Phe-Gln-Arg-Asn-Arg-Lys-Aca-Aca-Cys: 96 (SEQ ID NO: 9)
Cys-Aca-Aca-Thr-Trp-Tyr-Lys-Ile-Ala-Phe-Gln-Arg: 17 (SEQ ID NO: 10)
Phe-Gln-Arg-Asn-Arg-Lys-Aca-Aca-Cys: 13 (SEQ ID NO: 11)
Cys-Aca-Aca-Thr-Trp-Tyr-Lys-Ile-Ala: 7 (SEQ ID NO: 12)

The coating of culture surfaces made of polystyrene precoated with bovine serum albumin (BSA) with thiol peptides is disclosed in the prior art (see DE 198 18098 (Merck Patent GmbH), Ex. 2). The coating of PMMA surfaces with acrylate peptides is also described in DE 198 18098, Ex. 3.

The invention claimed is:

1. A compound of formula I $$B-Q-X_1 \qquad \qquad I$$

in which

B is a bioactive, cell adhesion-mediating molecule of formula (i), (ii) (SEQ ID NO 1), (iii) (SEQ ID NO 2), (iv) (SEQ ID NO 3), (v) (SEQ ID NO 4), (vi) (SEQ ID NO 5), or (vii) (SEQ ID NO 6),

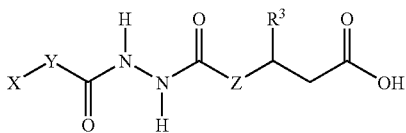
(i)

Thr-Trp-Tyr-Lys-Ile-Ala-Phe-Gln-Arg-Asn-Arg-Lys
(ii)

Trp-Tyr-Lys-Ile-Ala-Phe-Gln-Arg-Asn-Arg-Lys
(iii)

Tyr-Lys-Ile-Ala-Phe-Gln-Arg-Asn-Arg-Lys
(iv)

Thr-Trp-Tyr-Lys-Ile-Ala-Phe-Gln-Arg-Asn-Arg
(v)

Thr-Trp-Tyr-Lys-Ile-Ala-Phe-Gln-Arg-Asn
(vi)

Thr-Trp-Tyr-Lys-Ile-Ala-Phe-Gln-Arg
(vii), wherein
X is H$_2$N—C(=NH)—NH, Het-NH—, H$_2$N—C(=NH)—, A-C(=NH)—NH— or Het-,
Y is (CH$_2$)$_n$—,

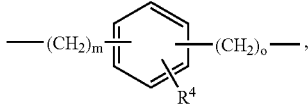

—(CH$_2$)$_s$—CH(R$^4$)—(CH$_2$)$_t$— or —(CH$_2$)$_p$Het$^1$-(CH$_2$)$_q$—,
Z is N—R$^2$ or CH—R$^2$,
R$^2$ is H or alkyl having 1 to 4 C atoms,
R$^3$ is H, Ar, Het or A,
R$^4$ is H, A, Ar, OH, OA, OAr, arylalkyl, Hal, CN, NO$_2$, CF$_3$ or OCF$_3$,
A is COOH, NH$_2$ or alkyl having 1-6 C atoms, which is unsubstituted or substituted by COOH or NH$_2$,
Ar is phenyl which is unsubstituted or mono-, di- or trisubstituted by A, OH, NH$_2$, OA, CF$_3$, OCF$_3$, CN, NO$_2$ or Hal, which can be substituted by a phenyl which is mono-, di- or trisubstituted by A, OH, OA, OCF$_3$, CN, NO$_2$ or Hal in such a way that an unsubstituted or substituted biphenyl results,
Hal is F, Cl, Br or I,
Het is a saturated, partly or completely unsaturated mono- or bicyclic heterocyclic radical having 5 to 10 ring members, where 1 to 3 N and/or an S or O atom(s) can be present and the heterocyclic radical can be mono- or disubstituted by CN, Hal, OH, NH$_2$, COOH, OA, CF$_3$, A, NO$_2$, Ar or OCF$_3$,
Het$^1$ is a 5- or 6-membered aromatic heterocycle having 1 to 4 N and/or S atoms, which can be unsubstituted or mono- or disubstituted by F, Cl, Br, A, OA or OCF$_3$,
n is 4, 5 or 6,
m, o, p, and q are 0, 1 or 2,
s and t are 0, 1, 2, 3, 4, 5;
Q is absent or is of formula (xvii), (xviii), (xix), (xx), (xxi), or (xxii),

| | |
|---|---|
| [CO—(CH$_2$)$_x$—NH—]$_m$, | (xvii) |
| [CO—CH$_2$—(O—CH$_2$CH$_2$)$_y$—NH—]$_m$, | (xviii) |
| [CO—(CH$_2$)$_z$—CO—] | (xix) |
| [NH—(CH$_2$)$_z$—NH—] | (xx) |
| [CO—CH$_2$—(OCH$_2$CH$_2$)$_y$—O—CH$_2$—CO—] | (xxi) |
| [NH—CH$_2$CH$_2$—(OCH$_2$CH$_2$)$_y$—NH—] | (xxii) | or a combination thereof,
m in each case independently of one another is 1 to 20,
x is 1 to 12,
y is 1 to 50, and
z is 1 to 12,
X$_1$ is an anchor molecule of formula (viii), (ix), (x), (xi), (xii), (xiii) or (xiv),

| | |
|---|---|
| —CO—CH=CH$_2$ | (viii) |
| —CO—(CH$_2$)$_{1-20}$—CO—CH=CH$_2$ | (ix) |
| —CO—(CH$_2$)$_{1-20}$—SH | (x) |
| —CO—CH(NH$_2$)—CH$_2$—SH | (xi) |
| —NH—(CH$_2$)$_{1-20}$—CO—CH=CH$_2$ | (xii) |
| —NH—(CH$_2$)$_{2-20}$—SH | (xiii) |
| —NH—CH(CO$_2$H)—CH$_2$—SH | (xiv), | where
in the case of the compounds with anchor molecules (viii) to (xi), a free amino group of the group B is linked by forming a peptide bond with a free carboxyl group of the spacer molecule Q or of the anchor molecule X$_1$, or a free amino group of the radical Q is linked by forming a peptide bond with a free carboxyl group of the radical X$_1$ is linked to one another, and
in the case of the compounds with anchor molecules (xii) to (xiv), a free carboxyl group of the group B is linked by forming a peptide bond with a free amino group of the spacer molecule Q or of the anchor molecule X$_1$, or a free carboxyl group of the radical Q is linked by forming a peptide bond with a free amino group of the radical X$_1$,
or a salt thereof.

2. A compound according to claim 1, in which Q is of formula (xvii), (xviii), (xix), (xx), (xxi), or (xxii),

| | |
|---|---|
| [CO—(CH$_2$)$_x$—NH—]$_m$, | (xvii) |
| [CO—CH$_2$—(O—CH$_2$CH$_2$)$_y$—NH—]$_m$, | (xviii) |
| [CO—(CH$_2$)$_z$—CO—] | (xix) |
| (NH—(CH$_2$)$_z$—NH—] | (xx) |
| [CO—CH$_2$—(OCH$_2$CH$_2$)$_y$—O—CH$_2$—CO—] | (xxi) |
| [NH—CH$_2$CH$_2$—(OCH$_2$CH$_2$)$_y$—NH—] | (xxii) | or a combination thereof,
in which
m in each case independently of one another is 1 to 8,
x is 1 to 5,
y is 1 to 6 and
z is 1 to 6.

3. A compound according to claim 1, which is a compound of formula a), b) (SEQ ID NO 7), c) (SEQ ID NO 8), d) (SEQ ID NO 9), e) (SEQ ID NO 10), e) (SEQ ID NO 11), or f) (SEQ ID NO 12),

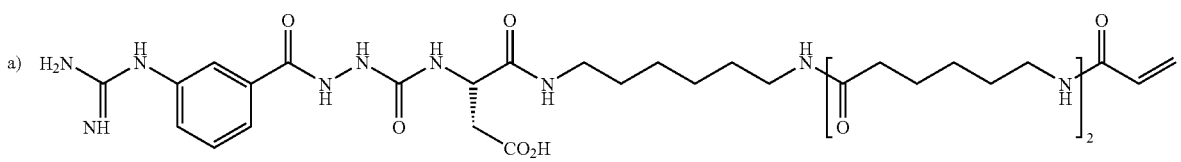

b) Thr-Trp-Tyr-Lys-Ile-Ala-Phe-Gln-Arg-Asn-Arg-Lys-Aca-Aca-Cys c) Cys-Aca-Aca-Thr-Trp-Tyr-Lys-Ile-Ala-Phe-Gln-Arg-Asn-Arg-Lys

-continued d) Lys-Ile-Ala-Phe-Gln-Arg-Asn-Arg-Lys-Aca-Aca-Cys e) Cys-Aca-Aca-Thr-Trp-Tyr-Lys-Ile-Ala-Phe-Gln-Arg f) Phe-Gln-Arg-Asn-Arg-Lys-Aca-Aca-Cys g) Cys-Aca-Aca-Thr-Trp-Tyr-Lys-Ile-Ala.

4. A pharmaceutical composition comprising a compound according to claim 1 and a pharmaceutically acceptable carrier.

5. An implant, which is suitable for a human or an animal organ, consisting essentially of a carrier matrix and a layer of a bioactive, cell adhesion-mediating molecule of formula I according to claim 1 surrounding this matrix, wherein a covalent bond or adsorptive binding is present between the carrier matrix and the compound of formula I.

6. An implant according to claim 5, wherein the carrier matrix and/or its surface is a metal or a metal oxide.

7. An implant according to claim 5, wherein the carrier matrix and/or its surface is a polymer.

8. An implant according to claim 7, wherein characterized in that the polymer is polymethyl methacrylate, polyhydroxyethyl methacrylate or copolymers thereof.

9. A process for preparing a compound of the formula I according to claim 1, or a salt thereof, comprising:

conjugating via a peptide bond a bioactive molecule B, with protecting groups, and a spacer-anchor molecule ($Q-X_1$) or an anchor molecule ($X_1$) with protecting groups;

removing the protecting groups; and optionally converting a basic or acidic compound of the formula I into one of its salts by treating with an acid or base.

10. A method for treating a disorder, defect or inflammation caused by an implant, or for treating an osteolytic disorder, osteoporosis, thrombosis, cardiac infarct or arteriosclerosis or for the acceleration and strengthening of an integration process of an implant or of a biocompatible surface into a tissue, comprising administering to a patient in need thereof an effective amount of a compound according to claim 1.

11. A method of preparing an implant for a human or an animal organ comprising coating said implant with a compound of formula I according to claim 1, wherein the compound of formula I binds to the implant by covalent bond or by adsorptive binding.

* * * * *

UNITED STATES PATENT AND TRADEMARK OFFICE
CERTIFICATE OF CORRECTION

PATENT NO. : 7,276,482 B2  Page 1 of 1
APPLICATION NO. : 10/344668
DATED : October 2, 2007
INVENTOR(S) : Joerg Meyer It is certified that error appears in the above-identified patent and that said Letters Patent is hereby corrected as shown below:

Column 19, line 46, should have -- (xx) -- associated with formula "[NH-(CH$_2$)$_Z$-NH-]"
Column 20, line 22, reads "X$_1$ is linked to one another, and" should read -- X$_1$, and --
Column 20, line 38, reads "(NH-(CH$_2$)$_z$-NH-]" should read -- [NH-(CH$_2$)$_z$-NH-] --
Column 20, line 47, reads "1 to 6and" should read -- 1 to 6 and --
Column 21, lines 24-25, reads "wherein characterized in that the polymer" should read -- wherein the polymer --
Column 22, lines 19-20, reads "arteriosclerosis or" should read -- arteriosclerosis, or --

Signed and Sealed this

Eighth Day of April, 2008

JON W. DUDAS
*Director of the United States Patent and Trademark Office*